United States Patent [19]
Berg

[11] Patent Number: 5,972,172
[45] Date of Patent: Oct. 26, 1999

[54] SEPARATION OF 1,2,4-TRIMETHYLBENZENE FROM 1,2,3-TRIMETHYLBENZENE BY EXTRACTIVE DISTILLATION

[76] Inventor: Lloyd Berg, 1314 S. Third Ave., Bozeman, Mont. 59715

[21] Appl. No.: 08/771,520

[22] Filed: Dec. 23, 1996

[51] Int. Cl.⁶ .............................. B01D 3/40; C07C 7/08
[52] U.S. Cl. .............................. 203/57; 203/58; 203/60; 203/62; 203/64; 203/65; 585/807; 585/808; 585/860; 585/864; 585/865
[58] Field of Search .............................. 203/57, 60, 58, 203/59, 62, 64–65, 67, 69–70; 585/804–807, 808, 860, 864, 865

[56] References Cited

U.S. PATENT DOCUMENTS

| 3,987,120 | 10/1976 | Hosler | 203/35 |
| 4,021,311 | 5/1977 | Becker | 203/69 |
| 4,371,428 | 2/1983 | Montagna et al. | 203/58 |
| 4,596,655 | 6/1986 | Van Eijl | 203/58 |
| 4,615,771 | 10/1986 | Zimmerman et al. | 203/63 |
| 5,032,232 | 7/1991 | Lee et al. | 203/58 |
| 5,135,620 | 8/1992 | Brown | 203/60 |
| 5,720,857 | 2/1998 | Berg | 203/57 |

FOREIGN PATENT DOCUMENTS

| 1543119 | 9/1969 | Germany | 203/57 |
| 0019722 | 3/1975 | Japan | 203/57 |

*Primary Examiner*—Virginia Manoharan

[57] ABSTRACT

1,2,4-Trimethylbenzene is difficult to separate from 1,2,3-trimethylbenzene by conventional distillation or rectification because of the proximity of their boiling points. 1,2,4-trimethylbenzene can be readily separated from 1,2,3-trimethylbenzene by extractive distillation. Effective agents are 3-nitrotoluene, m-cresol and sulfolane.

1 Claim, No Drawings

SEPARATION OF 1,2,4-TRIMETHYLBENZENE FROM 1,2,3-TRIMETHYLBENZENE BY EXTRACTIVE DISTILLATION

FIELD OF THE INVENTION

This invention relates to a method for separating 1,2,4-trimethylbenzene from 1,2,3-trimethylbenzene by extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, | Relative Volatility | | | | | | | |
|---|---|---|---|---|---|---|---|---|
| Both Products | 1.02 | 1.1 | 1.2 | 1.3 | 1.4 | 1.5 | 2.0 | 3.0 |
| (Mole Fraction) | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 25 | 22 | 12 | 7 |
| 0.98 | 392 | 81 | 42 | 29 | 22 | 18 | 10 | 6 |
| 0.95 | 296 | 61 | 11 | 21 | 16 | 14 | 8 | 4 |
| 0.90 | 221 | 45 | 23 | 15 | 12 | 10 | 5 | 2 |

There are a number of commercial processes which produce complex mixtures of aromatic hydrocarbons in the cumene boiling range. Two of the close boiling found there are 1,2,4-trimethylbenzene and 1,2,3-trimethylbenzene which boil only seven degrees apart. A process to separate these two would enhance their value as pure compounds. The relative volatility between these two is only 1.3 which makes it difficult to separate them by conventional rectification.

Extractive distillation would be an attractive method of effecting the separation of these two if agents can be found that (1) will create a large apparent relative volatility among these two and (2) are easy to recover from the higher boiling compound. Table 2 shows the relative volatility required to obtain 99% purity. With an agent giving a relative volatility of 1.6, only 27 actual plates are required.

TABLE 2

Theoretical and Actual Plates Required vs. Relative Volatility for Terpene Separation

| Relative Volatility | Theoretical Plates Required At Total Reflux, 99% Purity | Actual Plates Required 75% Efficiency |
|---|---|---|
| 1.4 | 28 | 35 |
| 1.5 | 22 | 30 |
| 1.6 | 20 | 27 |

OBJECTIVE OF THE INVENTION

The object of this invention is to provide a process or method of extractive distillation that will enhance the relative volatility of 1,2,4-trimethylbenzene from 1,2,3-trimethylbenzene in their separation in a rectification column. It is a further object of this invention to identify organic compounds which in addition to the above contraints, are stable, can be separated from the 1,2,3-trimethylbenzene and recyled to the column with little decomposition.

SUMMARY OF THE INVENTION

The objects of this invention are provided by a process for separating 1,2,4-trimethylbenzene from 1,2,3-trimethylbenzene which entails the use of certain organic compounds as the agent in extractive distillation.

DETAILED DESCRIPTION OF THE INVENTION

I have discovered that certain organic compounds will greatly enhance the relative volatility between 1,2,4-trimethylbenzene and 1,2,3-trimethylbenzene and permit separation by rectification when employed as the agent in extractive distillation. Table 3 lists the compounds that I have found to be effective in separating 1,2,4-trimethylbenzene from 1,2,3-trimethylbenzene by extractive distillation. They are acetophenone, dioctyl phthalate, methyl n-amyl ketoxime, benzonitrile, 3-methoxyacetophenone, 3-nitrotoluene, butyrolactone, m-cresol, p-cresol, o-cresol, 3-ethyl phenol, 1,6-dimethyl phenol and sulfolane.

TABLE 3

Effective Extractive Distillation Agents
1,2,4-Trimethylbenzene From 1,2,3-Trimethylbenzene

| Compounds | Relative Volatility |
|---|---|
| None | 1.3 |
| Acetophenone | 1.4 |

TABLE 3-continued

Effective Extractive Distillation Agents
1,2,4-Trimethylbenzene From 1,2,3-Trimethylbenzene

| Compounds | Relative Volatility |
|---|---|
| Dioctyl phthalate | 1.5 |
| Methyl n-Amyl ketoxime | 1.4 |
| Benzonitrile | 1.4 |
| 3-Nitrotoluene | 1.45 |
| Butyrolactone | 1.45 |
| 3-Methoxyacetophenone | 1.4 |
| 1,6-Dimethyl phenol | 1.45 |
| m-Cresol | 1.45 |
| p-Cresol | 1.45 |
| o-Cresol | 1.4 |
| Sulfolane | 1.45 |
| 3-Ethyl phenol | 1.4 |

THE USEFULNESS OF THE INVENTION

The usefulness or utility of this invention can be demonstrated by referring to the data presented in Tables 1, 2 and 3. All of the successful agents show that 1,2,4-trimethylbenzene can be separated from 1,2,3-trimethylbenzene by means of extractive distillation and that the ease of separation as measured by relative volatility is considerable.

WORKING EXAMPLE

Example 1

Fifty grams of a 1,2,4-trimethylbenzene-1,2,4-trimethylbenzene mixture and fifty grams of m-cresol as the extractive distillation agent were charged to a vapor-liquid equilibrium still and refluxed for two hours. The vapor composition was 68.7% 1,2,4-trimethylbenzene and 31.3% 1,2,3-trimethylbenzene; the liquid composition was 60.1% 1,2,4-trimethylbenzene and 39.9% 1,2,3-trimethylbenzene. This a relative volatility of 1.45.

I claim:

1. A method for recovering 1,2,4-trimethylbenzene from a mixture of 1,2,4-trimethylbenzene and 1,2,3-trimethylbenzene which consists essentially of distilling a mixture of 1,2,4-trimethylbenzene and 1,2,3-trimethylbenzene in the presence of an extractive distillation agent, recovering the 1,2,4-trimethylbenzene as overhead product and obtaining the 1,2,3-trimethylbenzene and the extractive distillation agent as bottoms product, wherein said extractive distillation agent consists of one material selected from the group consisting of acetophenone, dioctyl phthalate, methyl n-amyl ketoxime, benzonitrile, 3-methoxyacetophenone, 3-nitrotoluene, butyrolactone, m-cresol, p-cresol, o-cresol, 3-ethyl phenol, 1,6-dimethyl phenol and sulfolane.

* * * * *